United States Patent
Godin et al.

(10) Patent No.: US 9,352,133 B2
(45) Date of Patent: May 31, 2016

(54) BALLOON CATHETERS WITH INCREASED COLUMN STRENGTH

(75) Inventors: Dominick Godin, Minneapolis, MN (US); Derek R. Wise, New Brighton, MN (US); John Blix, Maple Grove, MN (US); Richard C. Gunderson, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 3152 days.

(21) Appl. No.: 11/148,726

(22) Filed: Jun. 9, 2005

(65) Prior Publication Data
US 2007/0005092 A1      Jan. 4, 2007

(51) Int. Cl.
*A61M 29/00* (2006.01)
*A61M 25/10* (2013.01)
*A61M 25/00* (2006.01)

(52) U.S. Cl.
CPC ....... *A61M 25/1006* (2013.01); *A61M 25/0023* (2013.01); *A61M 2025/0063* (2013.01)

(58) Field of Classification Search
CPC ............. A61M 2025/0063; A61M 2025/0006; A61M 2025/1061; A61M 25/0023; A61M 25/1006; A61M 2025/0059; A61M 2025/0004
USPC .......... 606/192, 195; 604/104, 96.01, 103.09; 623/1.11
See application file for complete search history.

(56) References Cited

U.S. PATENT DOCUMENTS

| | | | |
|---|---|---|---|
| 4,024,873 A | 5/1977 | Antoshkiw et al. | |
| 4,261,339 A * | 4/1981 | Hanson et al. | 600/18 |
| 4,323,071 A | 4/1982 | Simpson et al. | |
| 4,327,709 A | 5/1982 | Hanson et al. | |
| 4,346,698 A * | 8/1982 | Hanson et al. | 600/18 |
| 4,638,805 A | 1/1987 | Powell | |
| 4,646,742 A | 3/1987 | Packard et al. | |
| 4,665,925 A | 5/1987 | Millar | |
| 4,689,041 A | 8/1987 | Corday et al. | |
| 4,702,252 A | 10/1987 | Brooks et al. | |
| 4,794,928 A | 1/1989 | Kletschka | |
| 4,819,751 A | 4/1989 | Shimada et al. | |
| 4,892,519 A | 1/1990 | Songer et al. | |
| 4,955,895 A | 9/1990 | Sugiyama et al. | |
| 4,960,410 A | 10/1990 | Pinchuk | |
| 5,032,113 A | 7/1991 | Burns | |

(Continued)

FOREIGN PATENT DOCUMENTS

EP    0 339 093 A1    11/1989

*Primary Examiner* — Katrina Stransky
(74) *Attorney, Agent, or Firm* — Seager, Tufte & Wickhem LLP

(57) ABSTRACT

An intravascular balloon catheter that may include, for example, a first elongate member having a proximal end, an opening at the distal end and a lumen therebetween, a balloon defining a cavity, the balloon having a proximal waist sealingly attached to the first elongate member proximal the distal end, a distal waist, and a tubular portion therebetween, a second elongate member having a proximal end, a distal end and a lumen therebetween, the second elongate member disposed in the first elongate member and sealingly attached to the balloon distal waist, and a stopper attached to the second elongate member and disposed in the balloon cavity distal the distal end of the first elongate member, the stopper having an outer profile that prevents movement of the first elongate member thereover the first elongate member having an inner diameter at the distal end large enough to permit the passage of fluid therethrough over the second elongate member.

15 Claims, 33 Drawing Sheets

(56) References Cited

U.S. PATENT DOCUMENTS

| | | | |
|---|---|---|---|
| 5,047,045 A | | 9/1991 | Arney et al. |
| 5,061,273 A | | 10/1991 | Yock |
| 5,085,636 A | | 2/1992 | Burns |
| 5,100,381 A | | 3/1992 | Burns |
| 5,127,887 A | | 7/1992 | Nuttall |
| 5,135,487 A | | 8/1992 | Morrill et al. |
| 5,156,594 A | * | 10/1992 | Keith ................ 604/103.09 |
| 5,176,637 A | | 1/1993 | Sagae |
| 5,176,698 A | | 1/1993 | Burns et al. |
| 5,195,696 A | | 3/1993 | Kee Dong |
| 5,226,889 A | | 7/1993 | Sheiban |
| 5,342,386 A | | 8/1994 | Trotta |
| 5,378,237 A | | 1/1995 | Boussignac et al. |
| 5,403,339 A | | 4/1995 | Nobuyoshi et al. |
| 5,423,754 A | * | 6/1995 | Cornelius et al. ............ 604/103 |
| 5,425,712 A | | 6/1995 | Goodin |
| 5,492,532 A | * | 2/1996 | Ryan et al. ............ 604/103.09 |
| 5,499,973 A | | 3/1996 | Saab |
| 5,501,759 A | | 3/1996 | Forman |
| 5,512,051 A | | 4/1996 | Wang et al. |
| 5,533,985 A | | 7/1996 | Wang |
| 5,545,209 A | | 8/1996 | Roberts et al. |
| 5,547,472 A | | 8/1996 | Onishi et al. |
| 5,587,125 A | | 12/1996 | Roychowdhury |
| 5,755,707 A | | 5/1998 | Miyagawa et al. |
| 5,759,191 A | | 6/1998 | Barbere |
| 5,769,819 A | | 6/1998 | Schwab et al. |
| 5,824,173 A | * | 10/1998 | Fontirroche et al. ............ 156/86 |
| 5,876,376 A | | 3/1999 | Schwab et al. |
| 5,882,347 A | | 3/1999 | Mouris-Laan et al. |
| 6,010,521 A | | 1/2000 | Lee et al. |
| 6,027,477 A | | 2/2000 | Kastenhofer |
| 6,066,157 A | * | 5/2000 | Barbere ................ 606/194 |
| 6,086,556 A | | 7/2000 | Hamilton et al. |
| 6,106,889 A | | 8/2000 | Beavers et al. |
| 6,117,140 A | | 9/2000 | Munsinger |
| 6,165,166 A | | 12/2000 | Samuelson et al. |
| 6,179,811 B1 | | 1/2001 | Fugoso et al. |
| 6,179,856 B1 | | 1/2001 | Barbere |
| 6,325,814 B1 | | 12/2001 | Euteneuer et al. |
| 6,375,637 B1 | | 4/2002 | Campbell et al. |
| 6,465,067 B1 | | 10/2002 | Wang et al. |
| 6,514,228 B1 | | 2/2003 | Hamilton et al. |
| 6,623,491 B2 | | 9/2003 | Thompson |
| 6,623,518 B2 | | 9/2003 | Thompson et al. |
| 6,702,802 B1 | * | 3/2004 | Hancock et al. ............ 604/524 |
| 6,706,010 B1 | | 3/2004 | Miki et al. |
| 6,786,886 B2 | | 9/2004 | Miller et al. |
| 6,786,918 B1 | | 9/2004 | Krivoruchko et al. |
| 6,923,787 B2 | | 8/2005 | Wang |
| 6,962,597 B2 | | 11/2005 | Goodin |
| 2003/0078612 A1 | * | 4/2003 | Goodin ................ 606/192 |
| 2003/0105426 A1 | * | 6/2003 | Jorgensen ................ 604/103.1 |
| 2003/0163082 A1 | | 8/2003 | Mertens |

\* cited by examiner

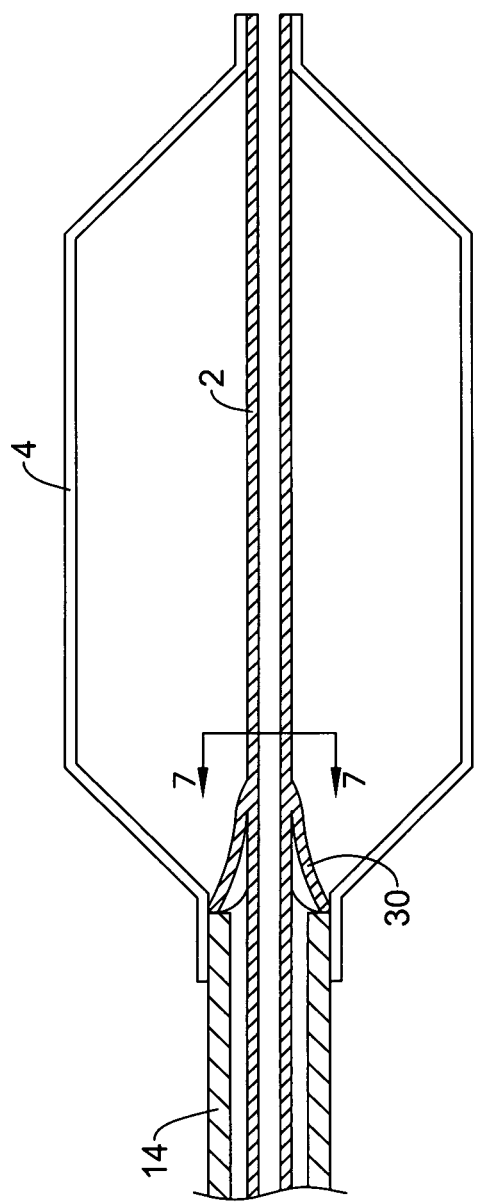
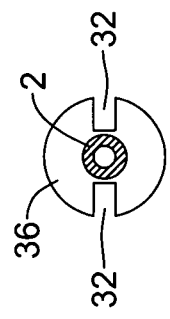
Figure 6
Figure 7

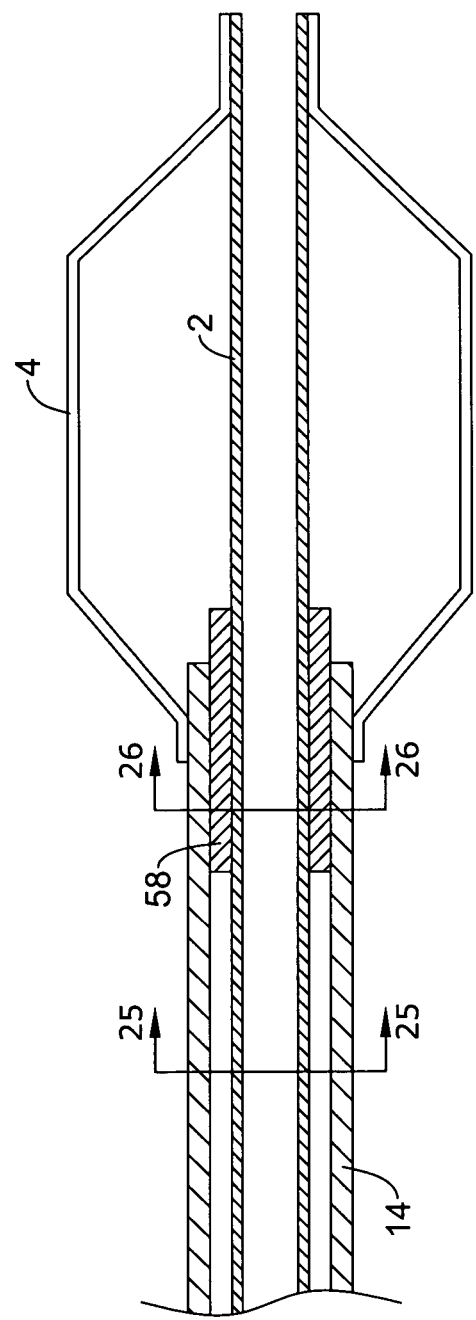

BALLOON CATHETERS WITH INCREASED COLUMN STRENGTH

FIELD OF THE INVENTION

The invention pertains to balloon catheters such as angioplasty or stent-delivery catheters and more particularly to coaxial embodiments having a guidewire lumen therethrough.

SUMMARY

One embodiment pertains to an intravascular balloon catheter having inner and outer catheter tubes with a a stopper attached to the inner tube and disposed in the balloon cavity distal the distal end of the outer tube, the stopper having an outer profile that prevents movement of the outer tube thereover while permiting flow of inflation fluid to the balloon cavity. The catheter may include one or more orifices in the outer tube proximal the first elongate member distal end and distal the balloon proximal waist. The stopper may include two or more lobes that define gaps therebetween to allow fluid passage from the distal end of the first elongate member into the balloon cavity. Alternatively, the stopper may be a basket attached to the second elongate member and flaring proximally to define a cavity sized to receive the distal end of the first elongate member or a cap attached to the second elongate member and flaring proximally to define a cavity sized to receive the distal end of the first elongate member that may have one or more orifices in a side wall thereof. The stopper may be fixed to the outer tube and may have a proximal face sized to abut a distal face of the outer tube and prevent distal passage of the outer tube thereover. Alternatively, the inner tube may have a first outer diameter and a second larger outer diameter distal the first outer diameter, the second outer diameter proximal end disposed in the balloon cavity and sized to prevent passage of the outer tube thereover and there may be a taper or a step-wise transition between the first outer diameter and the second outer diameter. The proximal waist of the catheter may extend distally of the distal end of the outer tube and the stopper may be fixed to the inner and sized to abut a distal face of the outer tube and may have one or more or openings positioned to allow the passage of fluid from a proximal to a distal side thereof. The catheter may include a radiopaque marker having a profile, the radiopaque marker being fixed to the outer tube and disposed in the balloon cavity, wherein the stopper is slidable on the second elongate member and is disposed between a distal face of the outer tube and the radiopaque marker, the stopper having a proximal face sized to abut the distal face of the outer tube and prevent distal passage of the outer tube thereover and a distal face sized to abut the radiopaque marker and sized to prevent distal passage of the stopper over the radiopaque marker.

Another embodiment pertains to a balloon catheter having a a wire attached to the outer tube proximate the proximal end thereof and attached to the inner tube in the general area of the balloon. The wire may include a coil disposed around the inner tube proximal the distal attachment point, one or more attachment points between the wire and the inner tube proximal the distal attachment point, or a radiopaque marker attached to the inner tube and disposed in the balloon cavity, wherein the wire is attached to the inner tube at the radiopaque marker.

Another embodiment pertains to a balloon catheter having a coil slidably disposed about the inner tube in the balloon cavity, the coil attached proximally to the proximal balloon waist or the distal end of the outer tube and attached distally to the distal balloon waist. The coil may also be attached distally to the inner tube proximate the distal balloon waist.

Another embodiment pertains to a balloon catheter wherein the stopper is attached to both the outer and inner tube, and the stopper permits a first relative position between the outer and inner tube where the stopper has a first length and second relative position between the outer and inner tube where the stopper has a second length shorter than the first length, the stopper permitting fluid flow therethrough. The stopper may include a plurality of telescoping wire rings or a plurality of sliding segments connected to each other seriatim.

Another embodiment pertains to a balloon catheter where the balloon inner surface has a first texture thereon, the second elongate member outer surface has a second texture thereon, where the first and second textures interact when the balloon is deflated to prevent relative movement of the balloon and the inner tube. The first texture may include a plurality of bumps and the second texture may include a plurality of transverse ribs or zigzag ribs. In an alternative embodiment, the balloon inner surface and the second elongate member outer surface have a tacky adhesive thereon that prevents relative movement of the balloon and the second elongate member in the deflated condition Another embodiment pertains to a balloon catheter where an interference fit proximate the distal waist of the balloon prevents relative movement between the first and second elongate members. The outer surface of the inner tube may have an irregular profile that provides the inteference fit with the inner surface of the first elongate member, where the first elongate member outer surface and the second elongate member inner surface defining one or more fluid passageways that fluidly connect the balloon cavity to the proximal end of the catheter. For example the inner tube may have a hexagonal profile. The outer tube may have a reduced inner diameter proximate the balloon proximal waist.

In an alternative embodiment, the catheter may include an insert between the first and second elongate members proximate the balloon proximal waist, the insert providing the interference fit and providing fluid passage lumens to fluidly connect the balloon cavity and the catheter proximal end. The insert may have circular inner profile and a non-circular outer profile such as a polygonal or an elliptical outer profile. Alternatively the insert may have a circular outer profile, a proximal face, a distal face and one or more lumens therebetween.

Another embodiment pertains to a balloon catheter that includes at least one protrusion extending inward from the inner surface of the outer tube and at least one protrusion separate from the protrusion from the outer tube extending outward from the outer surface of the inner tube, the protrusions cooperatively engaged to prevent relative axial movement between the outer and inner tube. The protrusion from the outer tube may define a ring-shaped groove and wherein the at least one protrusion from the inner tube comprises one or more tabs which fit in the groove, the protrusions providing one or more gaps therebetween for fluid flow. The protrusion from the first elongate member may taper proximally and distally. The protrusion from the second elongate member may be a ring and wherein the at least one protrusions from the outer tube may be tabs between which the ring is confined. The tabs may be axially aligned. The at least one protrusion in the outer tube may be formed by indenting the wall thereof. The at least one protrusion in the inner tube may include a proximal ring and a distal ring. The proximal ring may taper proximally and the distal ring taper may taper distally.

BRIEF DESCRIPTION OF THE DRAWINGS

The invention may be more completely understood in consideration of the following detailed description of various embodiments of the invention in connection with the accompanying drawings in which:

FIG. 6 is a partial diagrammatic view of a balloon catheter.
FIG. 7 is a partial cross-sectional view of the balloon catheter of FIG. 6.
FIG. 24 is a partial cross-sectional view of a balloon catheter.

DETAILED DESCRIPTION

Reference is now made to the figures, in which like element numbers refer to like elements throughout.

Figure 1:
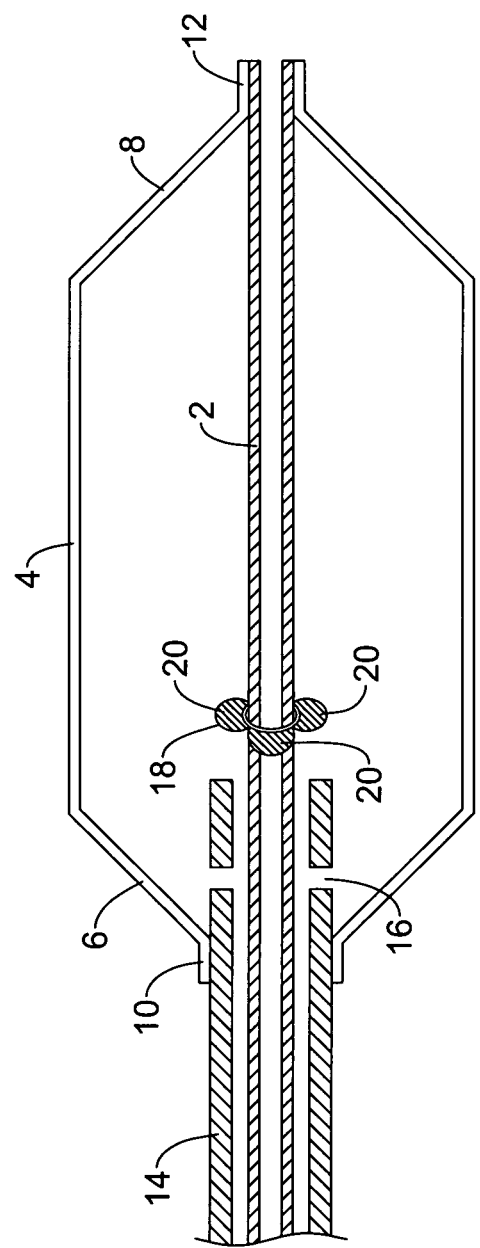
FIG. 1 is a partial diagrammatic view of a balloon catheter.

FIG. 1 is a partial diagrammatic side view of a balloon catheter having an inner tubular member 2 defining a guidewire lumen and an outer tubular member 14 defining an inflation lumen. A balloon 4 has a proximal waist 10 sealingly attached to the outer tubular member 14 and a distal waist 12 sealingly attached to the inner tubular member 12. The balloon defines an inflation cavity and may include a proximal cone 6 and a distal cone 8. The distal end of the outer tubular member may be spaced apart from the surface of the inner tubular member to permit the flow of inflation fluid therethrough. The opening formed by the outer tubular member distal end and the inner tubular member is annular, although it may have other shapes. For example, a balloon catheter may include a crescent-shaped opening. The distal end of the outer tubular member may extend into the balloon cavity and there may be one or more orifices 16 in the side wall of the outer tubular member. These orifices 16 may provide additional pathways for inflation fluid. A stopper 20 is affixed to the inner tubular member and is disposed in the balloon cavity. The stopper has an outer profile that prevents distal movement of the outer tubular member with respect to the inner tubular member but permits distal movement of the inner tubular member with respect to the outer tubular member. The stopper may be located further from or closer to the distal end of the outer tubular member as desired. For example, the stopper may abut the distal end of the outer tubular member. Stopper 20 includes several lobes 20 that define gaps therebetween that permit fluid flow to and from the distal end of the outer tubular member even when the stopper abuts the distal end thereof.

Figure 2:
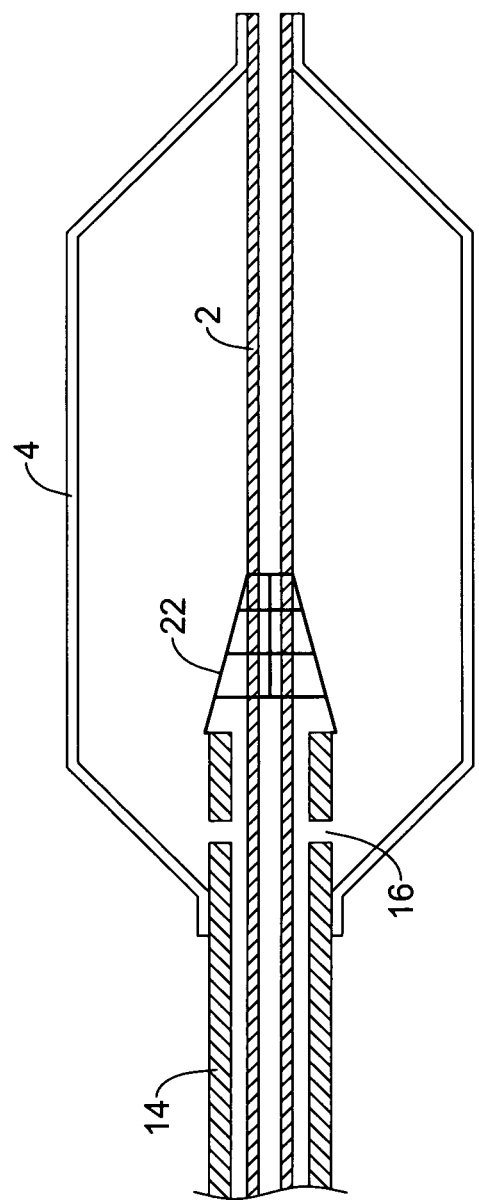
FIG. 2 is a partial diagrammatic view of a balloon catheter.

FIG. 2 is a partial diagrammatic view of a balloon catheter having an inner tubular member 2, a balloon 4 defining a balloon cavity and an outer tubular member 14. Attached to the inner tubular member is a basket 22. The basket has a proximal end that prevents the outer tubular member from moving distally relative to the inner tubular member but allows elongation of the balloon. The basket may include arms that can be compressed against the inner tubular member and are biased to spring out to the position shown. The basket may be made from metal, polymer resin or other suitable material. The outer tubular member may include orifices 16 that allow for inflation and deflation of the balloon.

Figure 3:
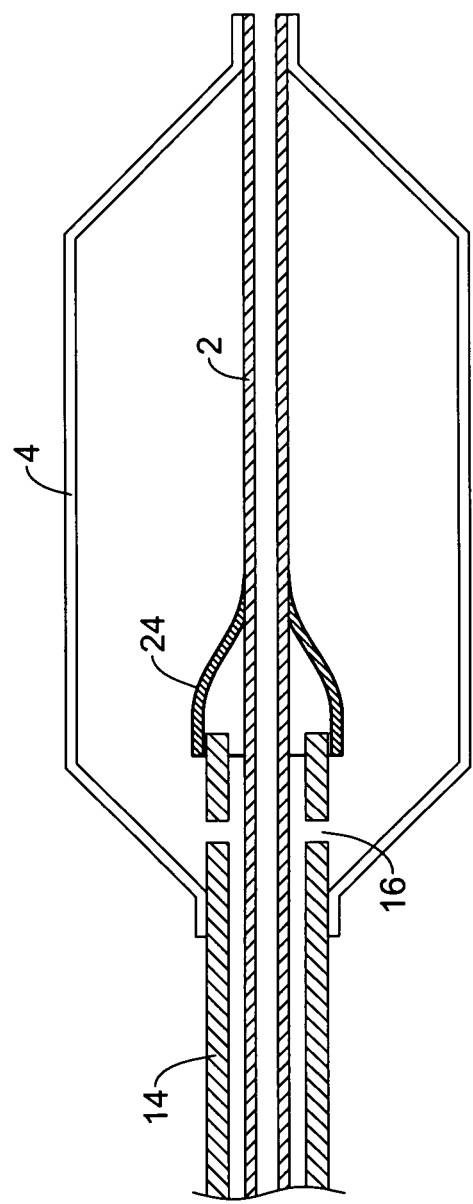
FIG. 3 is a partial diagrammatic view of a balloon catheter.

FIG. 3 is a partial diagrammatic view of a balloon catheter having an inner tubular member 2, a balloon 4 defining a balloon cavity and an outer tubular member 14. A stopper 24 is attached to the inner tubular member. The stopper may flare proximally to abut against or envelop the distal end of the outer tubular member and thus prevent the outer tubular member from moving distally relative to the inner tubular member while permitting balloon elongation. Orifices 16 may be included in the outer tubular member to provide a fluid flow path for inflation fluid.

Figure 4:
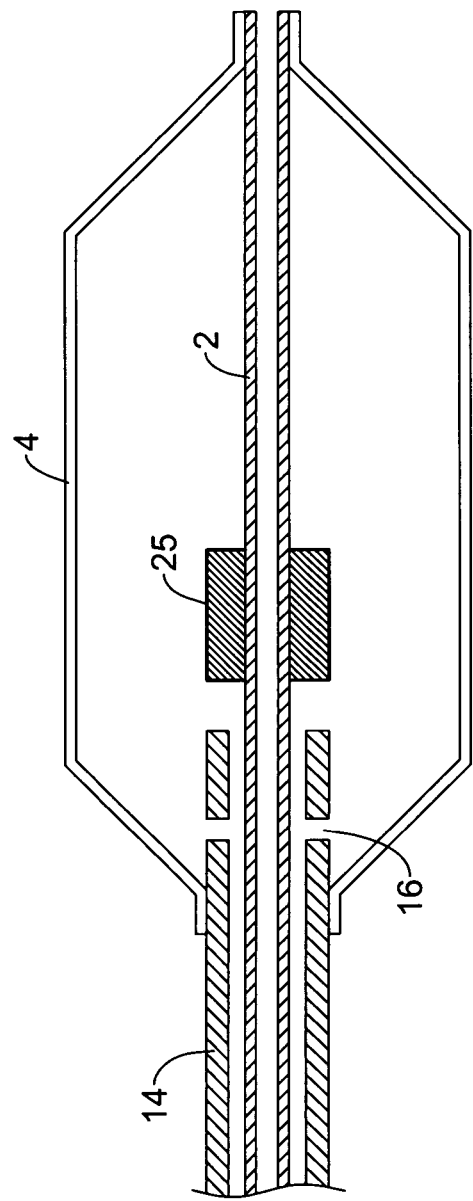
FIG. 4 is a partial diagrammatic view of a balloon catheter.

FIG. 4 is a partial diagrammatic view of a balloon catheter having an inner tubular member 2, a balloon 4 defining a balloon cavity and an outer tubular member 14. A stopper 25 is attached to the inner tubular member. The stopper is sized to abut against the distal end of the outer tubular member and prevent distal movement thereof. The stopper may include lumens extending from the proximal face to the distal face to provide a fluid flow path for the inflation fluid. Alternatively or in addition, orifices 16 may be provided in the distal end of the outer tubular member.

Figure 5:
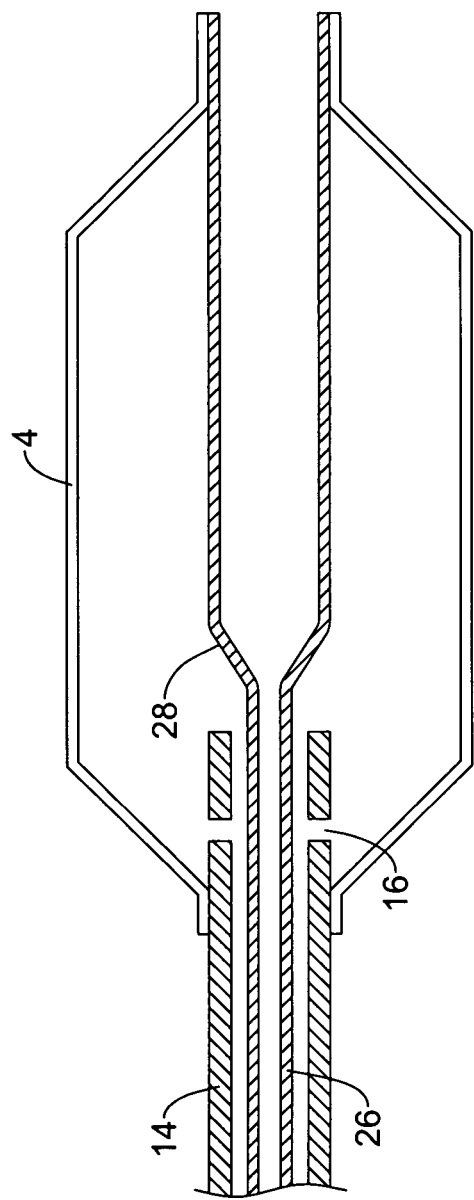
FIG. 5 is a partial diagrammatic view of a balloon catheter.

FIG. 5 is a partial diagrammatic view of a balloon catheter having an inner tubular member 26, a balloon 4 defining a balloon cavity and an outer tubular member 14. Inner tubular member 26 has a first outer profile and a second outer profile distal the first outer diameter and of greater size. The second outer profile is sized to prevent the distal passage of the outer tubular member thereon. The two sections of the inner tubular member may be joined by a flare 28, a step-wise increase, or other suitable configuration. The outer tubular member may include orifices 16 to provide an additional fluid flow path.

FIG. 6 is a partial side view of a balloon catheter having an inner tubular member 2, a balloon 4 defining an inflation cavity and an outer tubular member 14. The proximal waist of balloon 4 extends distally of the distal end of outer tubular member 14. A stopper 30 is attached to the inner tubular member and flares proximally to abut the distal end of the outer tubular member within the proximal balloon waist and prevent relative distal motion of the outer tubular member. As shown in FIG. 7, the stopper includes slots 32 to provide a fluid flow path. The stopper may have different configurations. For example, the stopper may be substantially cylindrical and have lumens extending longitudinally therethrough to provide an inflation fluid flow path.

Figure 8:
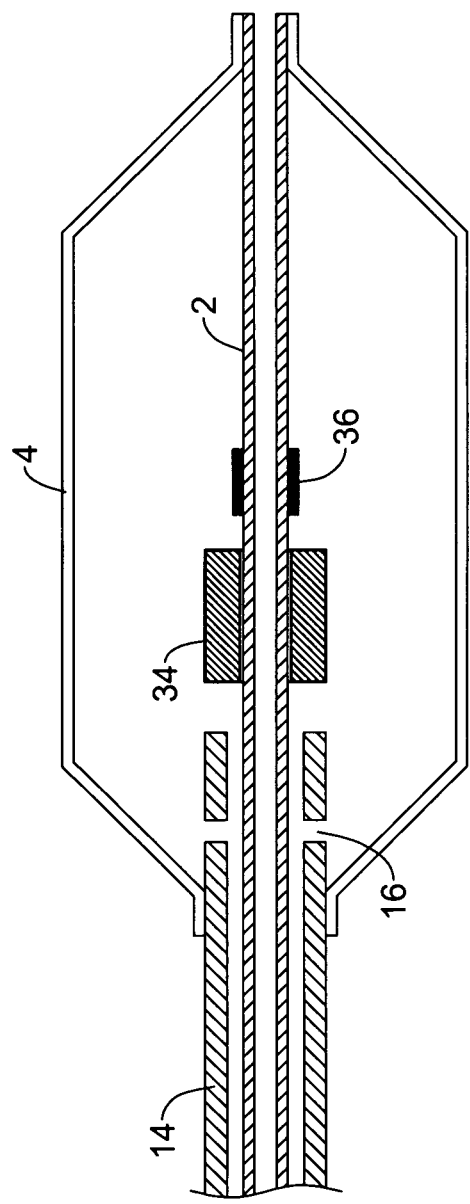
FIG. 8 is a partial cross-sectional view of a balloon catheter.

FIG. 8 is a partial diagrammatic view of a balloon catheter having an inner tubular member 2, a balloon 4 defining an inflation cavity and an outer tubular member 14. A slidable stopper 34 is disposed on the inner tubular member. Stopper 34 is prevented from moving distally beyond radiopaque marker 36 by the proximal profile of the marker. The distal end of the outer tubular member is prevented from moving distally beyond the stopper by the proximal profile of the stopper. Orifices 16 may be included to provide additional fluid flow paths.

Figure 9:
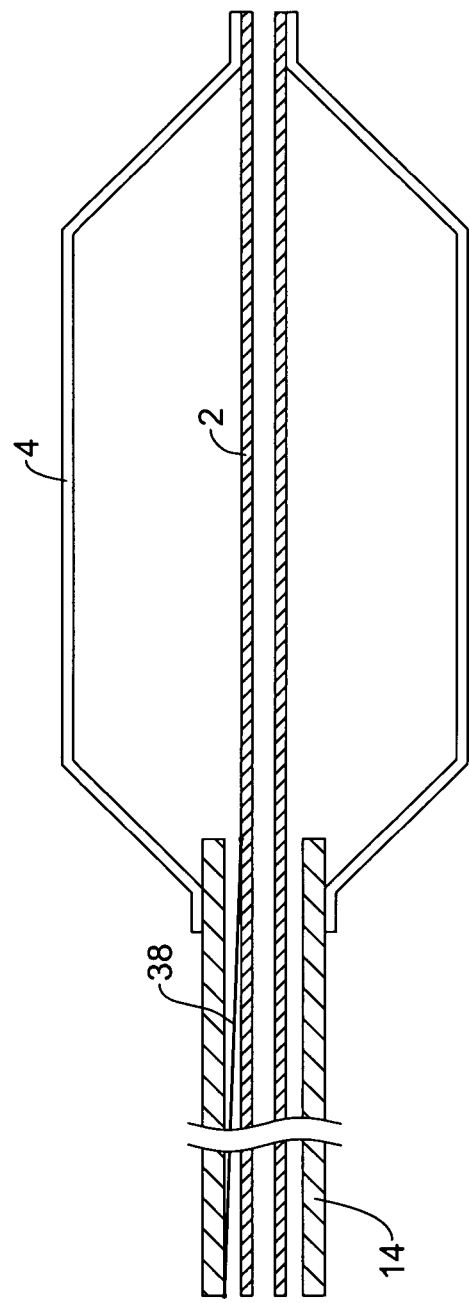
FIG. 9 is a partial cross-sectional view of a balloon catheter.
Figure 10:
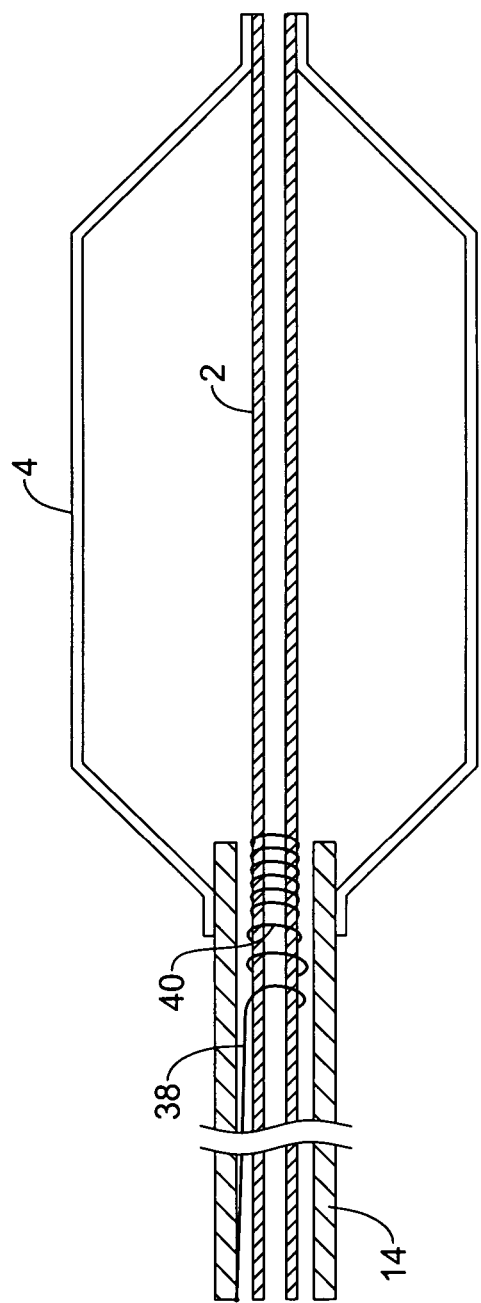
FIG. 10 is a partial cross-sectional view of a balloon catheter.
Figure 11:
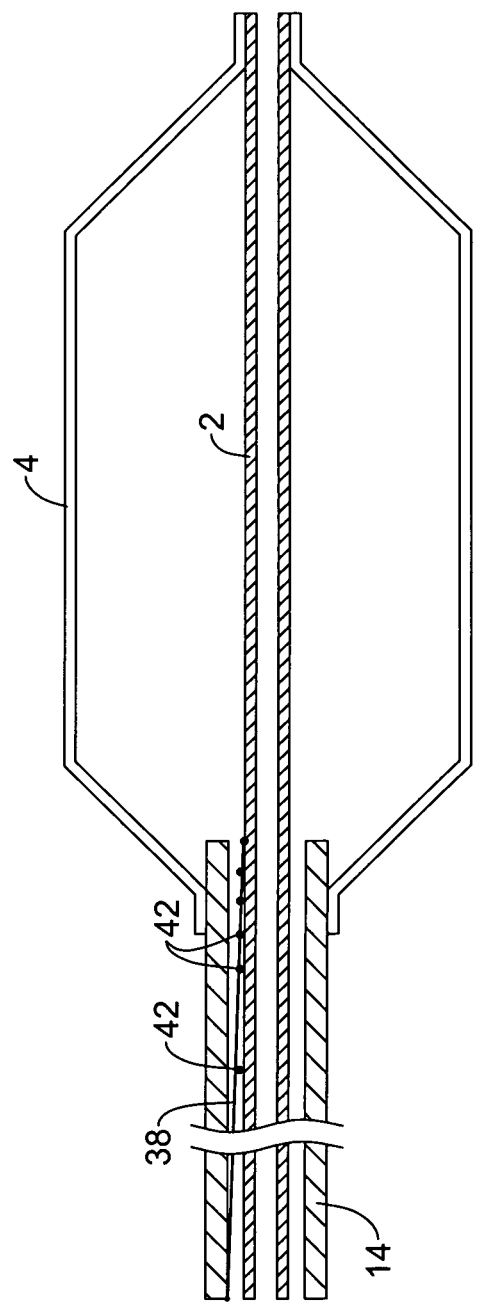
FIG. 11 is a partial cross-sectional view of a balloon catheter.
Figure 12:
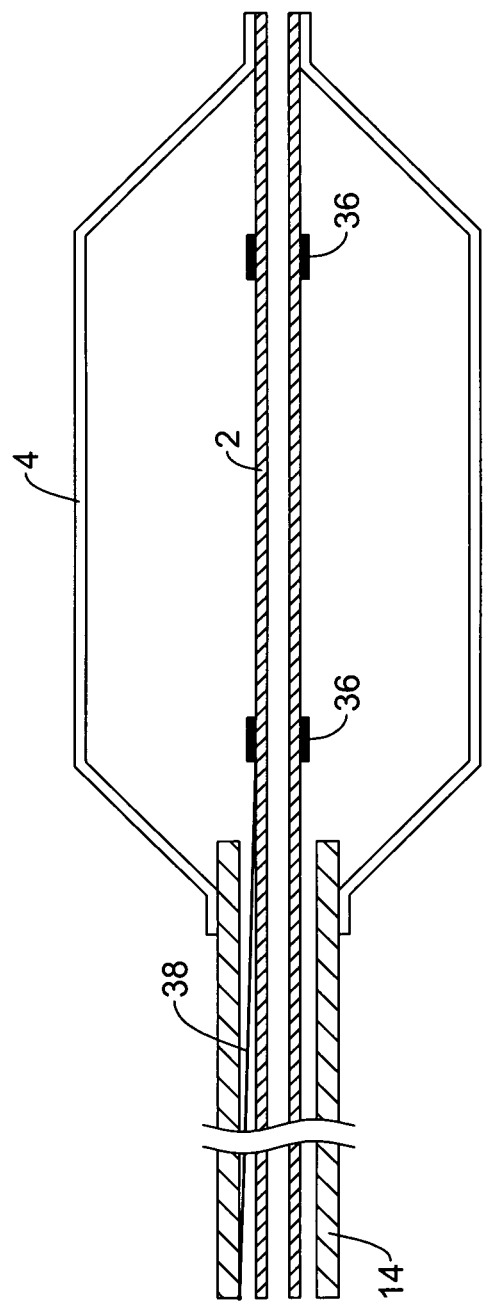
FIG. 12 is a partial cross-sectional view of a balloon catheter.

FIG. 9 is a partial side view of a balloon catheter having an inner tubular member 2, a balloon 4 defining an inflation cavity and an outer tubular member 14. A wire 38 disposed in the lumen of the outer tubular member and attached proximally to a proximal part of the outer tubular member and distal to the inner tubular member proximate the proximal waist of the balloon reduces relative movement of the inner and outer tubular members and may provide increased column strength. The term wire is used in this example embodiment and in all places in this application to denote a component having a length that is substantially greater than the transverse dimensions. The term wire does not imply a specific shape, cross-section or material. For example, a metal, a polymer resin or any suitable material may be used for wire 38. In an additional example, wire 38 could have a square, hollow, or variable cross-section. As shown in FIG. 10, the wire may have a coil 40. The coil is shown at the distal end of the wire but may be located elsewhere, such as further proximally. The coil is proximal the distal connection of the wire to the inner tubular member. The coil can compress along the longitudinal axis of the catheter to prevent relative movement of the inner and outer tubular members while permitting longitudinal expansion of the balloon. As shown in FIG. 11, wire 38 may have multiple distal attachment points 42 or may extend to a radiopaque marker 36 as shown in FIG. 12. Wire 38 may extend over only a portion of the catheter. For example, wire 38 may be attached proximally to a midpoint of the outer tubular member and distally to the inner tubular member at a radiopaque marker.

Figure 13:
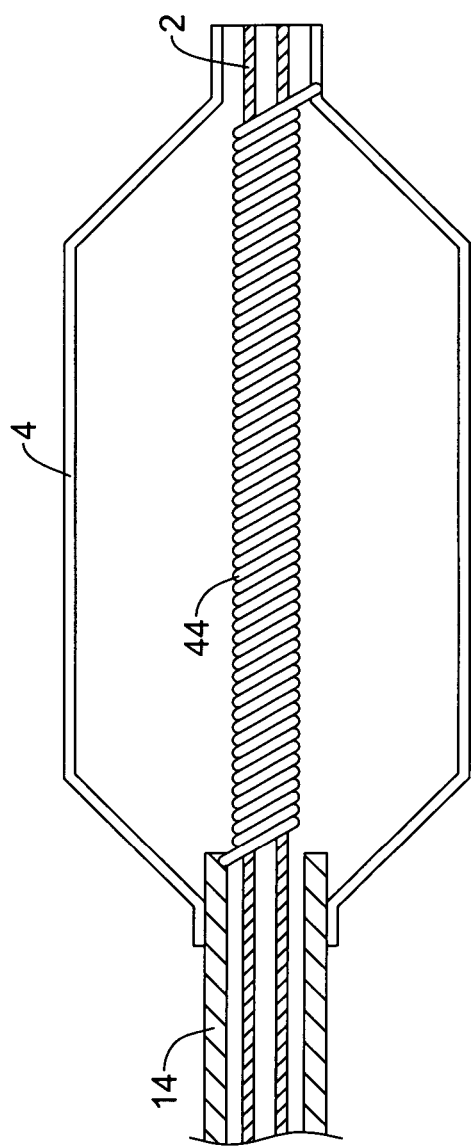
FIG. 13 is a partial cross-sectional view of a balloon catheter.
Figure 14:
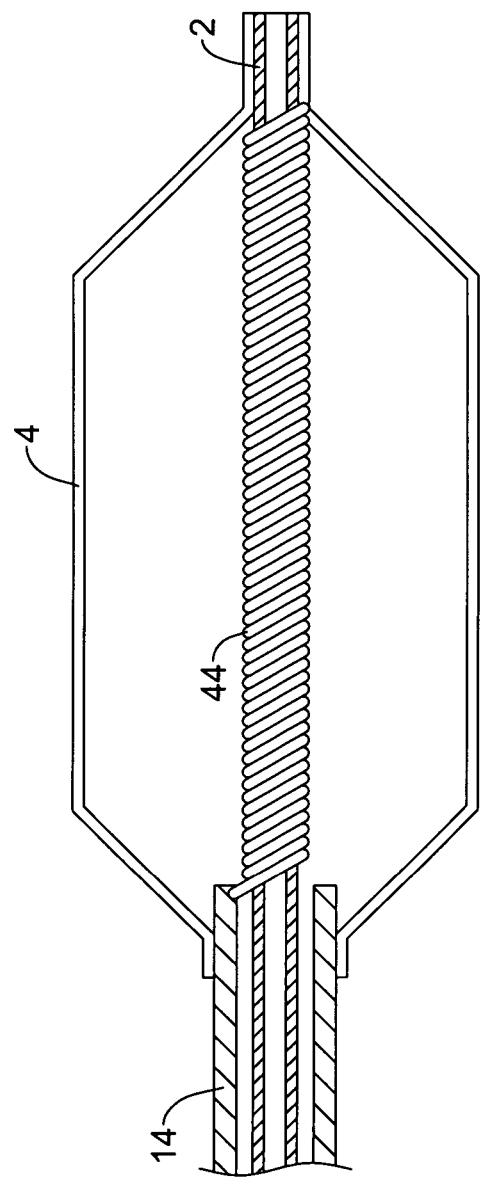
FIG. 14 is a partial cross-sectional view of a balloon catheter.

FIG. 13 is a partial diagrammatic view of a balloon catheter having an inner tubular member 2, a balloon 4 defining an inflation cavity and an outer tubular member 14. A closely wound coil 44 is disposed on the inner tubular member in the balloon cavity. The coil may be attached at a proximal end to the outer tubular member and at a distal end to the distal waist of the balloon. The coil provides columnar support to prevent distal movement of the outer tubular member from compressing the balloon while permitting the balloon to expand. The coil may be a spiral cut tube, a shaped wire coil or other suitable configuration. In the embodiment depicted in FIG. 14, the coil is also distally attached to the inner tubular member.

Figure 15:
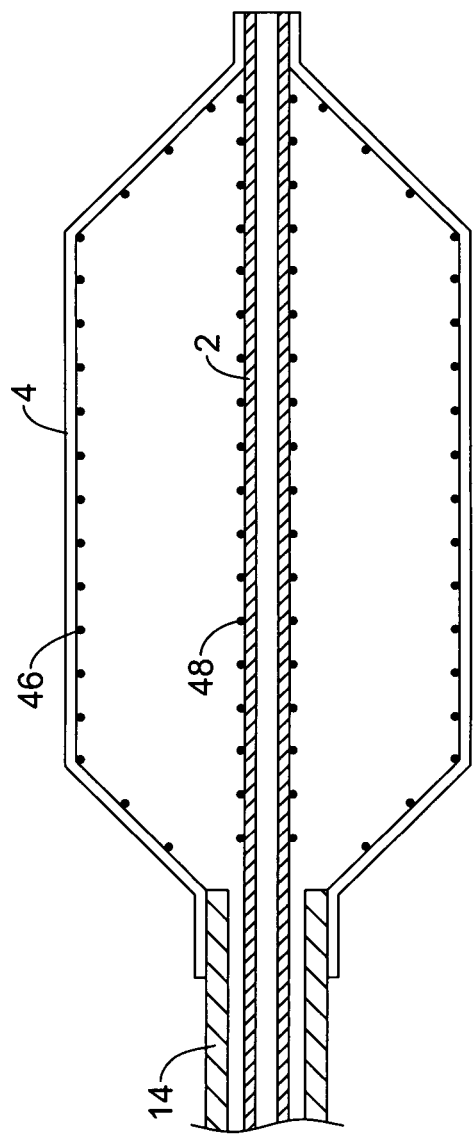
FIG. 15 is a partial cross-sectional view of a balloon catheter.
Figure 16:
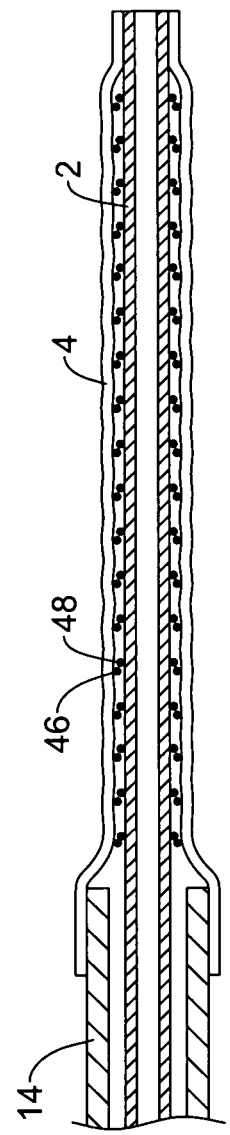
FIG. 16 is a partial cross-sectional view of the balloon catheter of FIG. 15 in a deflated condition.

FIG. 15 is a partial side view of a balloon catheter having an inner tubular member 2, a balloon 4 defining an inflation cavity and an outer tubular member 14 in an expanded position. FIG. 16 depicts the balloon catheter in a contracted position. The balloon catheter includes texture 46 on the inner surface of the balloon and texture 48 on the outer surface of the inner tubular member. When in the contracted position, textures 46 and 48 interact and mesh to prevent relative movement of the inner tubular member and the balloon. Textures 46 and 48 may be any compatible textures. For example, texture 48 may be a plurality of transverse or zigzag ribs and texture 46 may be small protrusions. Conversely, texture 46 may be transverse or zigzag ribs and texture 48 may be protrusions or ribs. Any suitable texture may be used.

Figure 17:
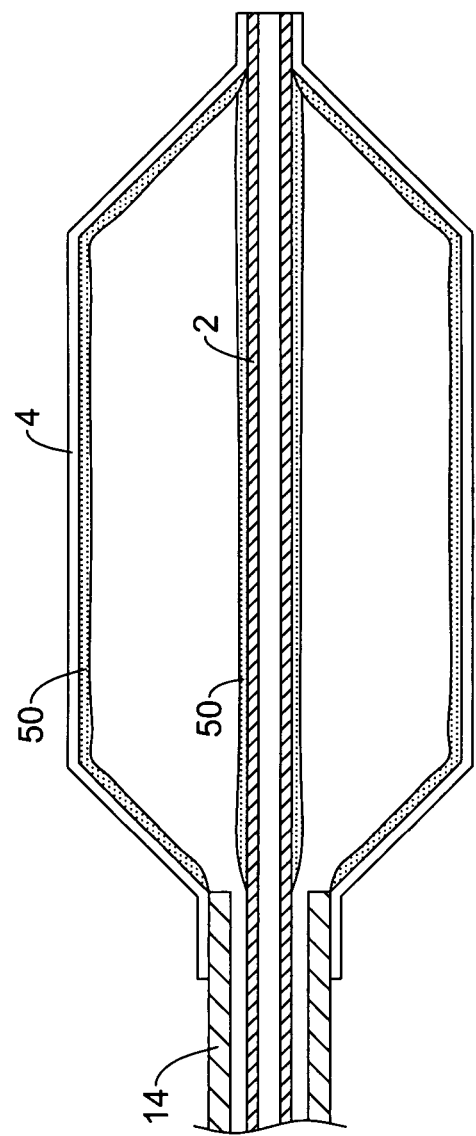
FIG. 17 is a partial cross-sectional view of a balloon catheter.
Figure 18:
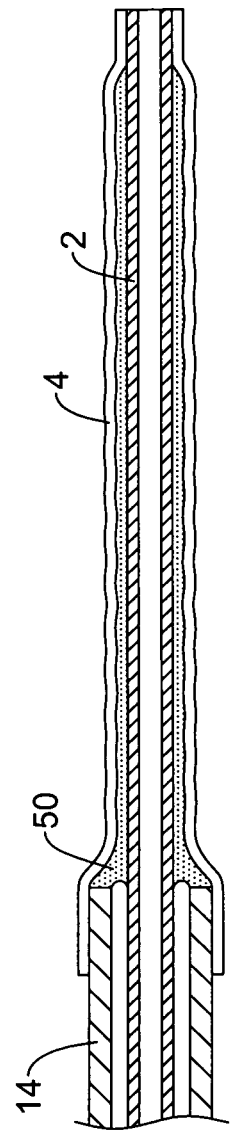
FIG. 18 is a partial cross-sectional view of the balloon catheter of FIG. 17 in a deflated condition.

FIG. 17 is a partial side view of a balloon catheter having an inner tubular member 2, a balloon 4 defining an inflation cavity and an outer tubular member 14 in an expanded position. FIG. 18 depicts the balloon catheter in a contracted position. On the inner surface of the balloon and the outer surface of the inner tubular member in the balloon cavity, a tacky adhesive 50 is disposed. Adhesive 50 is tacky but not so strong as to prevent inflation of the balloon and operates to prevent relative longitudinal motion between the balloon and the inner catheter. Adhesive 50 may be, for example, an uncured rubber gum. In some embodiments, adhesive 50 may lose its adhesive qualities once the balloon has been inflated. In some embodiments, adhesive 50 may be applied only to the balloon wall or only to the outer surface of the inner tubular member.

Figure 19:
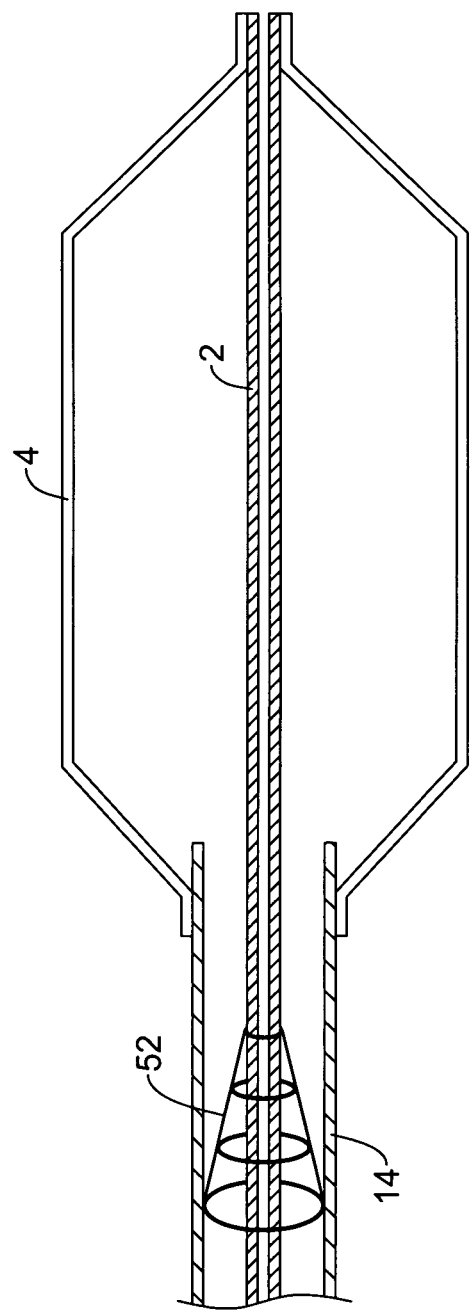
FIG. 19 is a partial cross-sectional view of a balloon catheter in a first state.
Figure 20:
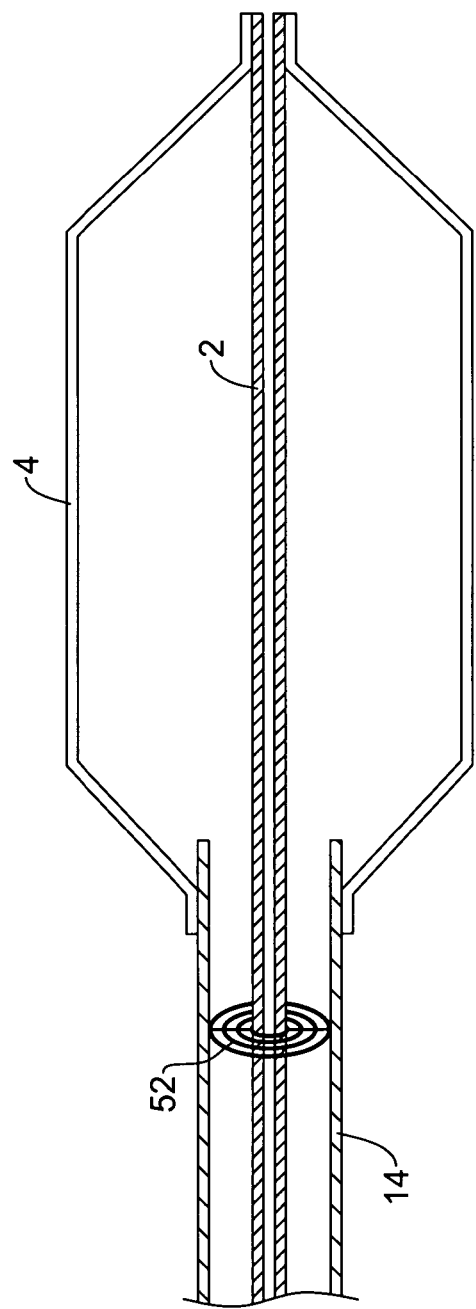
FIG. 20 is a partial cross-sectional view of the balloon catheter of FIG. 19 in a second state.
Figure 21:
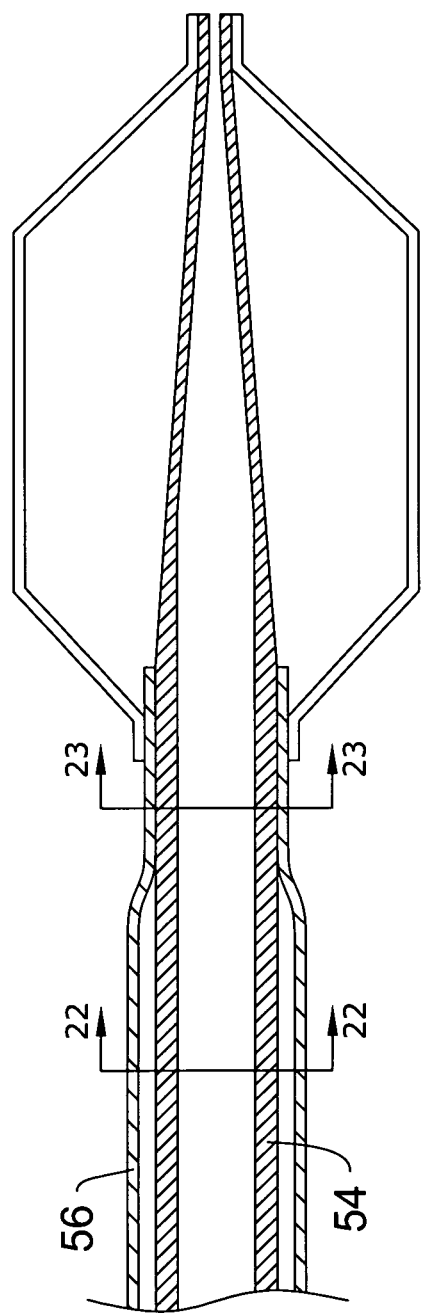
FIG. 21 is a partial cross-sectional view of a balloon catheter.

FIG. 19 is a partial side view of a balloon catheter having an inner tubular member 2, a balloon 4 defining an inflation cavity and an outer tubular member 14. A stopper 52 is attached to both the inner tubular member and the outer tubular member. The stopper includes several telescoping rings which collapse as shown in FIG. 20. Alternatively, the stopper includes a plurality of interlocking segments that slide into each other. The stopper permits only a limited range of relative movement between the inner tubular member and the outer tubular member.

Figure 22:
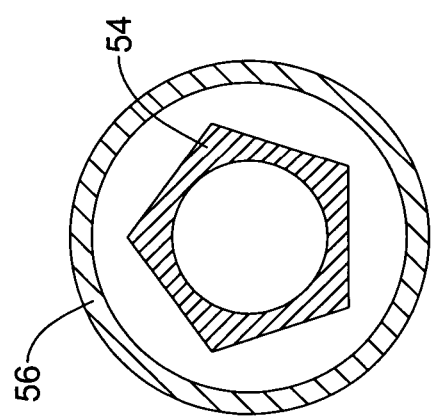
FIG. 22 is a cross-sectional view of the balloon catheter of FIG. 21.
Figure 23:
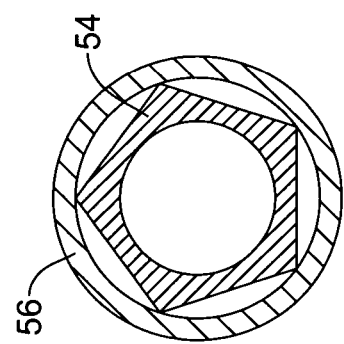
FIG. 23 is a cross-sectional view of the balloon catheter of FIG. 21.

FIG. 20 is a partial side view of a balloon catheter having an inner tubular member 54, a balloon 4 defining an inflation cavity and an outer tubular member 56. As can be seen in FIG. 22, inner tubular member 54 has a non-circular cross sectional profile. In this embodiment the profile is hexagonal, but other suitable profiles include but are not limited to pentagonal, gear-shaped, elliptical, and screw-shaped. The outer surface of the inner tubular member contacts the inner surface of the outer tubular member proximate the proximal end of the balloon. The inner catheter is in an interference fit with the outer catheter, preventing relative movement thereof. In other embodiments, adhesive or welding may be used to join the inner and outer catheters. The non-circular profile of the inner catheter ensures that one or more lumens remain open for the passage of the inflation medium, as can be seen in FIG. 23. In other embodiments, the outer catheter may have a non-circular inner profile that creates an interference fit with a substantially circular inner catheter. The outer catheter may have a reduced distal profile to engage the inner catheter.

Figure 26:
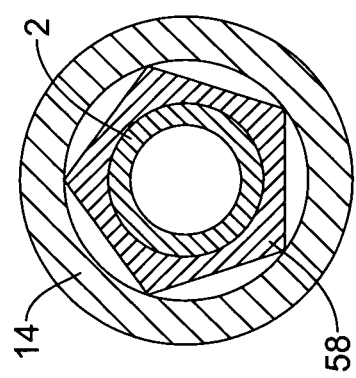
FIG. 26 is a cross-sectional view of the balloon catheter of FIG. 24.
Figure 25:
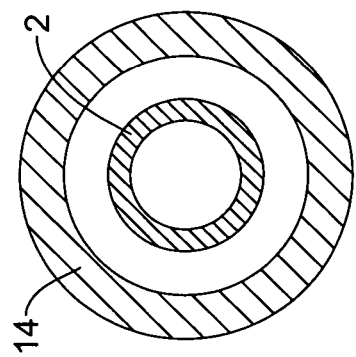
FIG. 25 is a cross-sectional view of the balloon catheter of FIG. 24.

FIG. 24 is a partial side view of a balloon catheter having an inner tubular member 2, a balloon 4 defining an inflation cavity and an outer tubular member 14. An insert 58 is disposed between the outer tubular member and the inner tubular member and prevents relative longitudinal movement between the two. The insert extends distally into the balloon cavity. Insert 58 may have an interference fit with one or both of the outer and inner tubular members or may be adhesively joined or welded to one or both of the outer and inner tubular members. Insert 58 has a non-circular outer profile as may be seen in FIG. 26. The profile of insert 58 is hexagonal, but many profiles are suitable, some of which have been described above. The profile of the insert provides lumens for the passage of inflation fluid to the balloon. In other embodiments, insert 58 has a non-circular inner profile. Circular and non-circular are terms used with respect to the balloon catheters depicted herein. A circular profile is a profile that may be coincident with the profile of one of the tubular members, all of which are shown herein as circular. However, non-circular tubular members may be used and in such cases, the profile of the insert may be modified to be used with the non-circular tubular member. In other words, the term circular is not intended to be so limiting.

Figure 27:
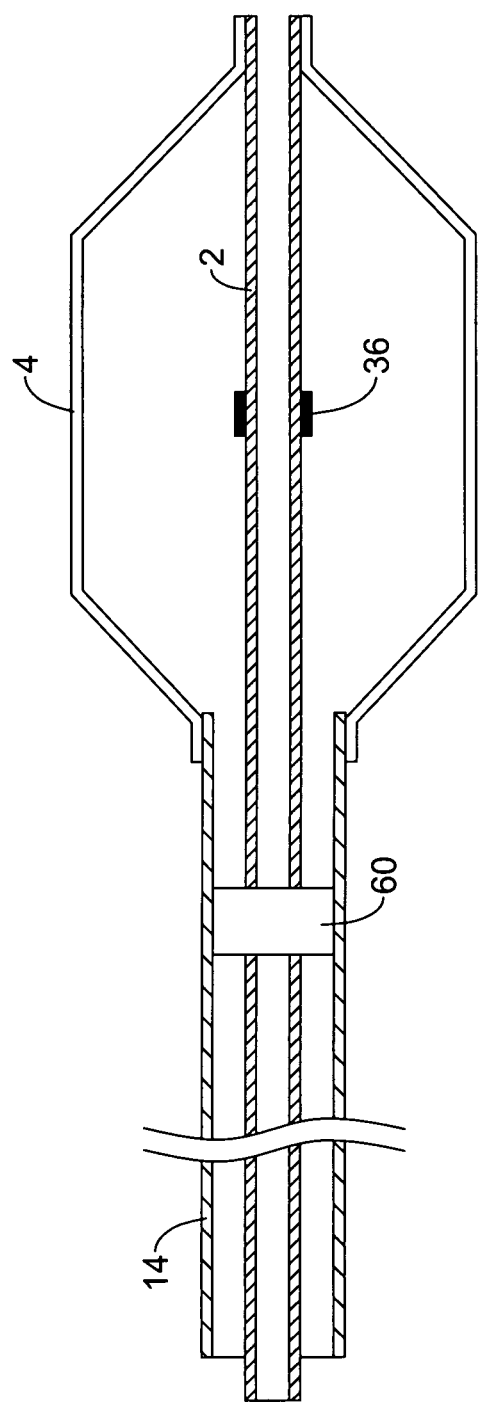
FIG. 27 is a partial cross-sectional view of a balloon catheter.
Figure 29:
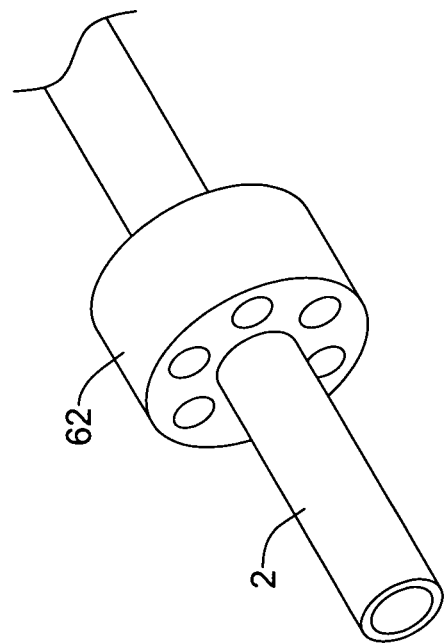
FIG. 29 is a perspective view of a catheter shaft.
Figure 28:
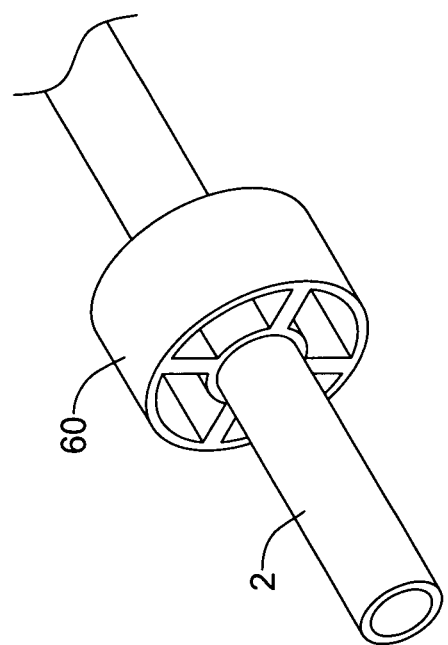
FIG. 28 is a perspective view of a catheter shaft.
Figure 31:
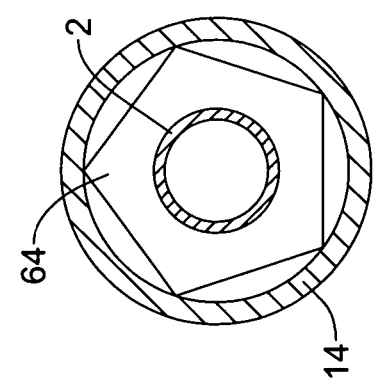
FIG. 31 is a cross-sectional view of a catheter shaft.
Figure 30:
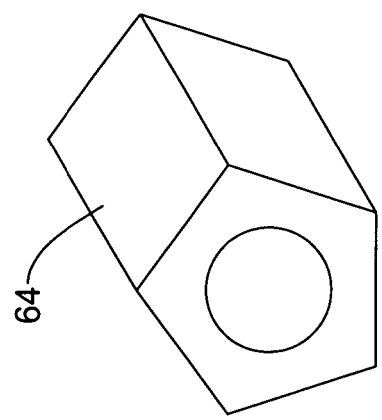
FIG. 30 is a perspective view of a spacer.
Figure 33:
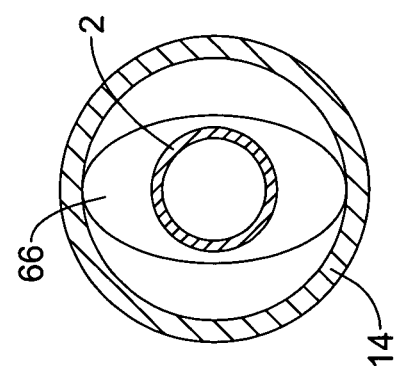
FIG. 33 is a cross-sectional view of a catheter shaft.
Figure 32:
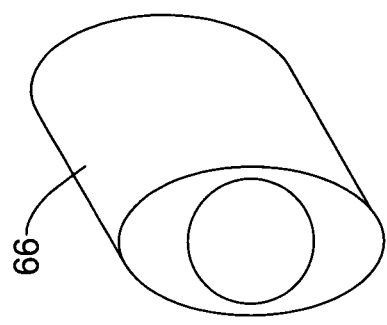
FIG. 32 is a perspective view of a spacer.

FIG. 27 is a partial side view of a balloon catheter having an inner tubular member 2, a balloon 4 defining an inflation cavity and an outer tubular member 14. An insert 60 is disposed between the outer tubular member and the inner tubular member and prevents relative longitudinal movement between the two. The insert is positioned proximally of the outer tubular member distal end, although other positions may be suited. For example, the insert may be placed at the outer tubular member distal end. FIGS. 28 and 29 are perspective views depicting example tubular members disposed on inner tubular members 2. Both insert 60 and insert 62 have circular inner and outer profiles and both have lumen patterns therethrough to provide a pathway for inflation fluid. FIG. 30 is a perspective view of an insert 64 having a noncircular hexagonal outer profile. FIG. 31 depicts a cross-sectional view of a balloon catheter having this insert therein. FIG. 32 is a perspective view of an insert 66 having a noncircular elliptical outer profile. FIG. 33 depicts a cross-sectional view of a balloon catheter having this insert therein. As can be readily inferred from these four example inserts, many inserts with varied profiles may be suitable.

Figure 34:
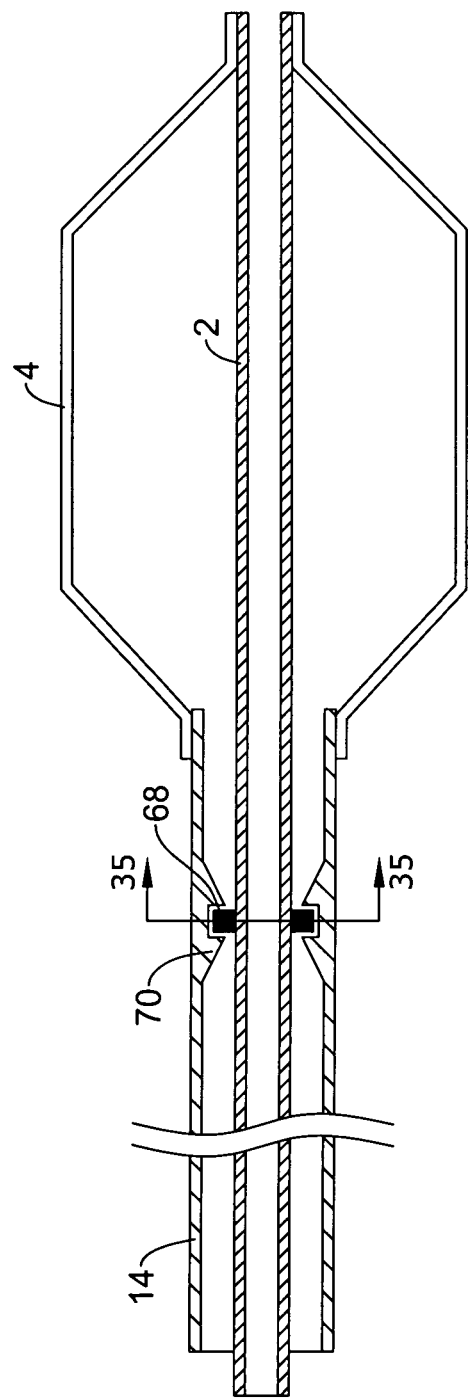
FIG. 34 is a partial cross-sectional view of a balloon catheter.
Figure 35:
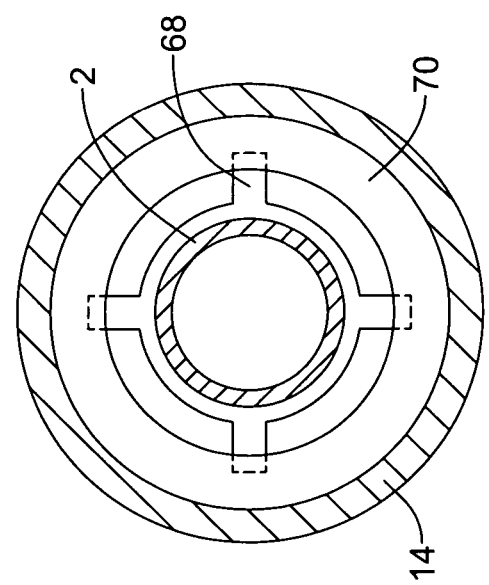
FIG. 35 is a cross-sectional view of the catheter shaft of FIG. 34.
Figure 36:
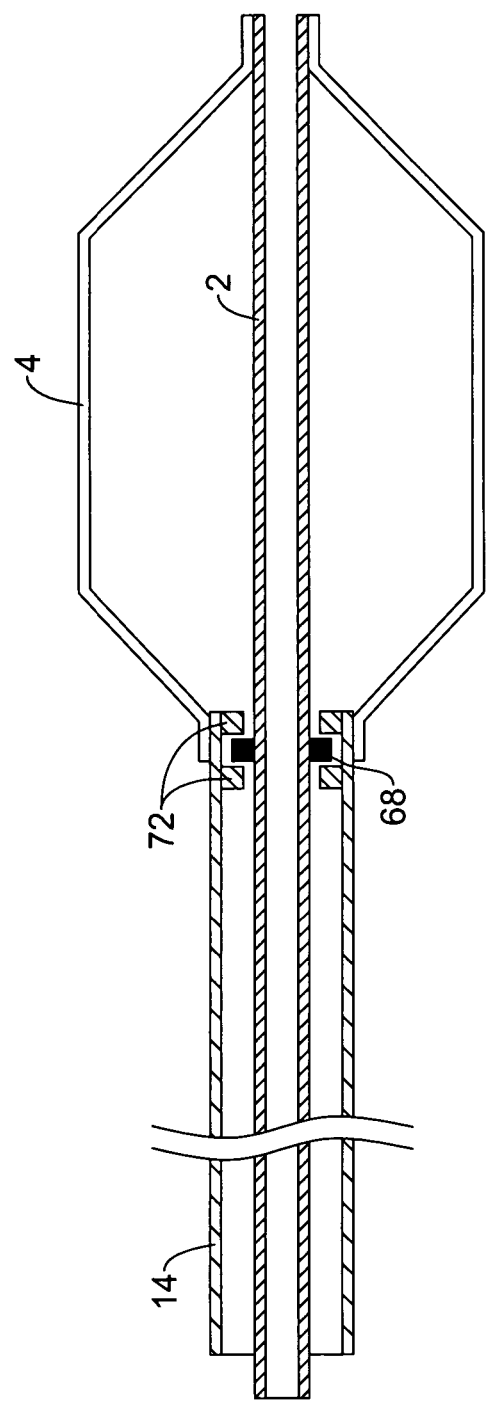
FIG. 36 is a partial cross-sectional view of a balloon catheter.
Figure 37:
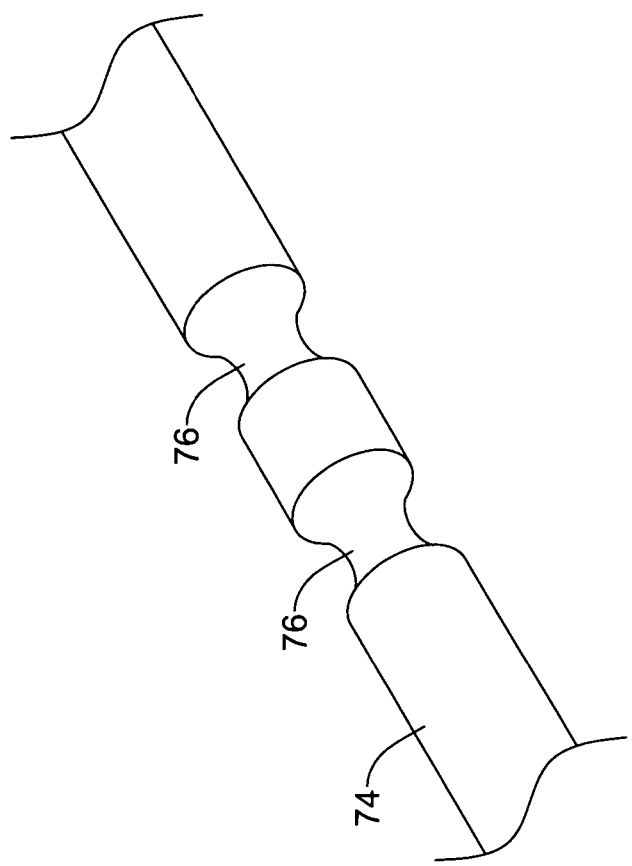
FIG. 37 is a side view of a catheter shaft.
Figure 38:
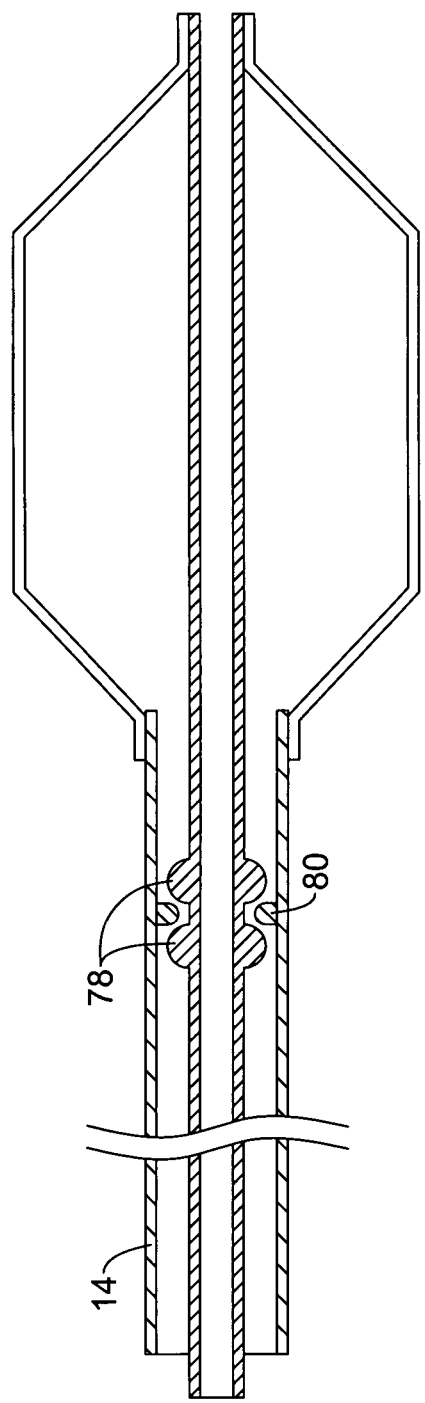
FIG. 38 is a partial perspective view of a catheter shaft.
Figure 39:
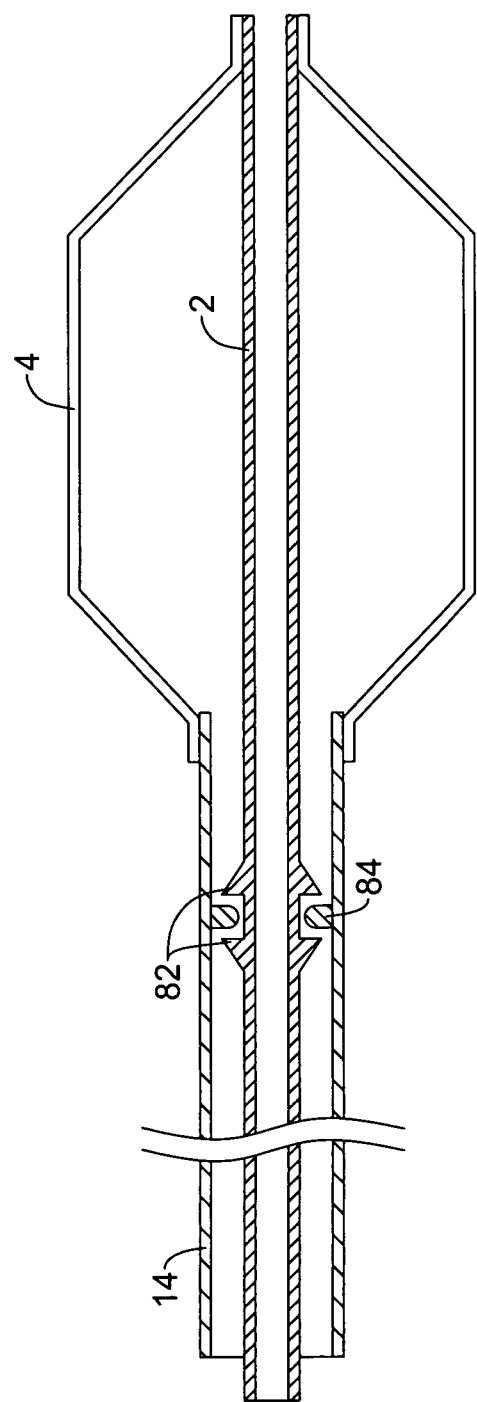
FIG. 39 is a partial perspective view of a catheter shaft.

FIG. 34 is a diagrammatic side view of a balloon catheter having an inner tubular member 2, a balloon 4 and an outer tubular member 14. A protrusion 68 is attached to the inner tubular member and is confined by a protrusion 70 attached to the outer tubular member. The inner catheter can rotate with respect to the outer catheter at this point, but has very limited proximal or distal relative motion. As can be seen from FIG. 35, protrusion 70 is a ring defining an annular groove. The ring may have proximal and distal tapers as shown. Protrusion 68 includes four tabs (though fewer or more tabs may be used) that are trapped in the annular groove. The combination of the protrusions does not fully occlude the inflation lumen, thereby providing the inflation fluid with a path to the balloon. Other embodiments may include variations of this. For example, one embodiment not pictured has a protrusion on the inner tubular member that is a ring defining an annular groove and a protrusion on the outer tubular member that has five tabs confined in the groove. FIG. 36 depicts an embodiment having a ring 68 on the inner tubular member confined by pairs of tabs 72 on the outer tubular members. Tabs 72 may or may not be axially aligned. FIG. 37 is a perspective view of an example outer tubular member 74. Protrusions may be created in outer tubular member 74 by forming indents 76 in the outer surface of the member. Such indents may be thermoformed, for example. FIG. 38 depicts a balloon catheter having rounded protrusions 78 on the inner tubular member forming a channel for confining protrusions 80 on the outer tubular member. Protrusions 80 are one, two or more beads disposed on the inner surface of the outer tubular member. FIG. 39 depicts a balloon catheter having tapered protrusions 82 defining a channel for confining protrusions 84. Protrusions 84 may be one, two or more tabs extending from the inner surface of the outer tubular member.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. None of the description in the present application should be read as implying that any particular element, step, or function is an essential element which must be included in the claim scope. Moreover, none of these claims are intended to invoke 35 U.S.C. §112, ¶6 unless the exact words "means for" are followed by a participle. The invention's scope is, of course, defined in the language in which the appended claims are expressed.

What is claimed is:
1. An intravascular balloon catheter, comprising:
   a first elongate member having a proximal end, an opening at the distal end and a lumen therebetween;
   a balloon defining a cavity, the balloon having a proximal waist sealingly attached to the first elongate member proximal the distal end of the first elongate member, a distal waist, and a tubular portion therebetween;
   a second elongate member having a proximal end, a distal end and a lumen therebetween, the second elongate member disposed in the lumen of the first elongate member and sealingly attached to the balloon distal waist; and
   a stopper attached to the second elongate member distal the distal end of the first elongate member and proximal the balloon distal waist, the stopper having an outer profile that prevents movement of the first elongate member thereover, the first elongate member having an inner diameter at the distal end large enough to permit the passage of fluid therethrough over the second elongate member;
   wherein the second elongate member is configured to move distally with respect to the first elongate member;
   wherein the proximal waist extends distally of the distal end of the first elongate member; and
   wherein the stopper is fixed to the second elongate member and sized to abut a distal face of the first elongate member;
   wherein when the stopper abuts the distal face of the first elongate member, fluid is not blocked from passing between the cavity of the balloon and the volume between the first and second elongate members;
   wherein the distal end of the first elongate member extends into the cavity of the balloon; and
   wherein proximate the distal end of the first elongate member, the first elongate member has a side wall containing one or more orifices.
2. The catheter of claim 1, wherein the stopper comprises two or more lobes, the lobes defining gaps therebetween to allow fluid passage from the distal end of the first elongate member into the balloon cavity.

3. The catheter of claim 1, wherein the stopper is a basket attached to the second elongate member and flaring proximally to define a cavity sized to receive the distal end of the first elongate member.

4. The catheter of claim 3, wherein the basket is movable between a first lower profile configuration and a second configuration where the basket flares proximally to define the cavity, and wherein the basket is biased to be in the second configuration.

5. The catheter of claim 1, wherein the stopper is a cap attached to the second elongate member and flaring proximally to define a cavity sized to receive the distal end of the first elongate member.

6. The catheter of claim 5, wherein the stopper comprises one or more orifices in a side wall thereof.

7. The catheter of claim 1, wherein the stopper is fixed to the first elongate member and has a proximal face sized to abut a distal face of the first elongate member and prevent distal passage of the first elongate member thereover.

8. The catheter of claim 1, wherein the second elongate member has a first outer diameter and a second larger outer diameter distal the first outer diameter, the second outer diameter proximal end disposed in the balloon cavity and sized to prevent passage of the first elongate member thereover.

9. The catheter of claim 8, wherein the second elongate member comprises a taper between the first outer diameter and the second outer diameter.

10. The catheter of claim 8, wherein the second elongate member comprises a step-wise transition between the first outer diameter and the second outer diameter.

11. The catheter of claim 1, wherein the stopper comprises a wall having one or more or openings positioned to allow the passage of fluid therethrough.

12. The catheter of claim 1, further comprising a radiopaque marker having a profile, the radiopaque marker being fixed to the second elongate member and disposed in the balloon cavity, wherein the stopper is slidable on the second elongate member and is disposed between a distal face of the first elongate member and the radiopaque marker, the stopper having a proximal face sized to abut the distal face of the first elongate member and prevent distal passage of the first elongate member thereover and a distal face sized to abut the radiopaque marker and sized to prevent distal passage of the stopper over the radiopaque marker.

13. The catheter of claim 1, wherein the stopper is attached to the first elongate member and the second elongate member, the stopper permitting a first relative position between the first and second elongate members where the stopper has a first length and second relative position between the first and second elongate members where the stopper has a second length shorter than the first length, the stopper permitting fluid flow therethrough.

14. The catheter of claim 13, wherein the stopper comprises a plurality of telescoping wire rings.

15. The catheter of claim 13, wherein the stopper comprises a plurality of sliding segments connected to each other seriatim.

* * * * *